United States Patent
Peterson (10) Patent No.: US 7,153,297 B2
(45) Date of Patent: Dec. 26, 2006

(54) UNIVERSAL ATTACHMENT MECHANISM FOR ATTACHING A TRACKING DEVICE TO AN INSTRUMENT

(75) Inventor: Thomas H. Peterson, Wilmington, MA (US)

(73) Assignee: GE Medical Systems Global Technolgoy Company, LLC, Waukesha, WI (US)

( * ) Notice: Subject to any disclaimer, the term of this patent is extended or adjusted under 35 U.S.C. 154(b) by 241 days.

(21) Appl. No.: 10/699,960

(22) Filed: Nov. 3, 2003

(65) Prior Publication Data
US 2005/0096536 A1 May 5, 2005

(51) Int. Cl.
*A61B 17/00* (2006.01)

(52) U.S. Cl. .......................................... 606/1

(58) Field of Classification Search ................ 128/870, 128/877, 883; 600/424, 102
See application file for complete search history.

(56) References Cited

U.S. PATENT DOCUMENTS

| | | | |
|---|---|---|---|
| 4,190,224 A | | 2/1980 | LeBlanc et al. |
| 5,099,577 A | * | 3/1992 | Hutt ............................ 30/101 |
| 5,380,338 A | * | 1/1995 | Christian .................... 606/130 |
| 5,987,960 A | | 11/1999 | Messner et al. |
| 6,358,199 B1 | * | 3/2002 | Pauker et al. ............... 600/114 |

FOREIGN PATENT DOCUMENTS

| | | |
|---|---|---|
| DE | 83 507 C | 2/1895 |
| DE | 44 38 633 A1 | 5/1996 |
| DE | 299 12 742 U1 | 11/1999 |
| WO | WO 02/061371 | 8/2002 |

OTHER PUBLICATIONS

French search report for App No.FR 0411389 dated Feb. 14, 2006.

* cited by examiner

*Primary Examiner*—Linda C. M. Dvorak
*Assistant Examiner*—Alex Toy
(74) *Attorney, Agent, or Firm*—McAndrews, Held & Malloy, Ltd.; Peter J. Vogel; Michael A. Dellapenna

(57) ABSTRACT

An attachment mechanism for attaching a component to a cylindrical instrument having a centerline. The attachment mechanism includes legs having respective first and second ends. The legs are pivotally connected relative to each other at the first ends such that the second ends of the legs can be pivoted away from each other and toward each other. The legs are configured to be connected to the component. Each leg has an engagement piece at its second end. The engagement piece is configured to engage around the cylindrical instrument. Each engagement piece is oriented toward its corresponding leg at a fixed angle. The orientation of each of the engagement pieces to its corresponding leg positions the engagement pieces to contact the instrument at contact points in order that the component is located at a known and constant distance from the centerline regardless of the diameter of the instrument.

20 Claims, 6 Drawing Sheets

UNIVERSAL ATTACHMENT MECHANISM FOR ATTACHING A TRACKING DEVICE TO AN INSTRUMENT

BACKGROUND OF THE INVENTION

The present invention relates to a mechanism for attaching a tracking system component to an instrument. More particularly, certain embodiments of the present invention relate to a universal attachment mechanism for attaching a surgical tracking localizer to a cylindrical surgical instruments of varying diameters.

During surgical operations, it is beneficial to be able to track the direction, trajectory and distal tip of a surgical instrument, such as a drill bit, into a patient's body in order to ensure that the instrument is directed into the appropriate point in the body. Therefore, surgical tracking systems have been developed that are able to display and monitor the direction, trajectory and distal tip of a surgical instrument relative to an image of the patient's body.

One system used for surgical tracking is an electromagnetic tracking system. In a typical electromagnetic tracking system, the area of the patient's body where surgery is to take place is imaged using an imaging technology such as the MRI, ultrasound, X-ray, CT scan or any other appropriate imaging device. The scanned images are stored in a computer system and are displayed on a screen during the surgical procedure. Alternatively, some systems, known generally as imageless systems, use a computer model in place of the scanned image. Data points are taken from the actual patient in the operating room and the model is morphed to provide an image representing the actual patient. A transmitter that emits an electromagnetic field is then secured to the patient's body proximate the area of the patient's body where surgery is to take place in a fixed and known position to the surgical site. The instrument that is to be tracked during surgery has a receiver attached thereto that receives the electromagnetic signals from the transmitter. The transmitter and receiver are both connected to communicate with the computer that displays the image. The computer translates the location of the transmitter to an equivalent point on the image. Then, by monitoring the signals sent from the transmitter to the receiver as the instrument is used in surgery, the computer is able to track the movement of the instrument relative to the transmitter, and thus the surgical site, and transpose the movement to the image. Therefore, medical personnel may closely track the positioning and progress of the instrument within the patient's body during surgery by examining the image.

Alternatively, in some electromagnetic systems, a receiver is placed on the patient and the instrument, and a field transmitter is placed proximate the patient. The receivers and transmitter are connected to the computer, and the computer is then able to track the movements of the instrument on an image similarly to the system using just a single receiver.

There are other surgical tracking systems besides electromagnetic tracking systems, such as optical tracking systems. Optical tracking systems typically use light emitting diodes (LEDs) that are attached to the surgical instrument and to the body portion of the patient on which the surgical procedure is to be performed. The LEDs are tracked by a camera unit (sometimes referred to as a digitizer). The output of the camera unit is used by the computer to recreate the movement of the instrument on the image.

In order for a surgical tracking system to work, the tracking device attached to the instrument, whether it be a receiver, transmitter or an LED, must be calibrated with the trajectory and distal tip of the instrument. When the trajectory and distal tip of the instrument are known relative to the tracking device, then the computer can effectively determine the location of the instrument. Calibration of a tracking device is greatly simplified by placing the device a constant distance from the trajectory (the centerline) of the rotating shaft of the instrument being tracked. In this fashion, a simple calibration would be required to calibrate the position of the distal tip of the instrument. If the trajectory of the cylindrical tool is in a known relationship to the tracking device, then only calibration of the instrument's distal tip is required for fully determining the location of the instrument. Methods of accurately locating the distal tip are well known in the art.

The tracking device may be custom-integrated into the surgical instrument, however, such a practice involves considerable development costs and time to integrate each individual application. Additionally, many new surgical applications require tracking of cylindrical tools of varying diameters such as awls, drills, drill guides, probes, and various drivers. Therefore, universal systems for calibrating the trajectory and distal tip of a tool have been developed.

For example, one system used for tracking an interchangeable rotating cylindrical instrument, such as a drill bit, is the tool calibrator described in U.S. Pat. No. 5,987,960 to Messner. In Messner, there are tracking devices on the instrument handle and on two interlocking blocks. The interlocked blocks have oppositely aligned V-shaped grooves that receive the instrument head therein such that the tracking devices on the blocks are a known distance from the centerline of the instrument. Thus, the tracking devices on the blocks can communicate with a computer system to calculate the trajectory of the instrument. The instrument has a first point that is in a known position relative to the tracking devices on the instrument. One of the blocks has a second point that is in a known position relative to the tracking devices on the blocks and a flat surface on the block. The distal tip of the instrument is positioned to engage the flat surface on the block, then the tracking devices on the instrument and the blocks communicate with the computer to calculate the position of the distal point with respect to a reference frame of the instrument.

However, the calibration system of Messner suffers from its own drawbacks. There is the added expense of integrating tracking devices onto the instrument handle in addition to having tracking devices on the blocks. Additionally, it is a cumbersome practice to have to attach the blocks to each new instrument head used during the surgery, calibrate the instrument with the blocks, and then remove the blocks. Furthermore, the Messner system cannot be used with an instrument having an attachment at the distal tip.

Therefore, a need exists for an improved attachment mechanism for attaching a tracking device to any number of different cylindrical instruments.

BRIEF SUMMARY OF THE INVENTION

Certain embodiments of the present invention include an attachment mechanism for attaching a component to a cylindrical instrument having a centerline. The attachment mechanism includes legs having respective first and second ends. The legs are pivotally connected relative to each other at the first ends such that the second ends of the legs can be pivoted away from each other and toward each other. The legs are configured to be connected to the component. Each leg has an engagement piece at its second end. The engagement piece is configured to engage around the cylindrical instrument. Each engagement piece is oriented toward its corresponding leg at a fixed angle. The orientation of each of the engagement pieces to its corresponding leg positions the engagement pieces to contact the instrument at contact points in order that the component is located at a known and constant distance from the centerline regardless of the diameter of the instrument.

Certain embodiments of the present invention include a computer assisted surgical tracking system. The system includes a surgical drill having a cylindrical instrument with a centerline, an electromagnetic receiver, a computer that displays an image of a surgical site, and an attachment mechanism. The attachment mechanism has legs having respective first and second ends. The legs are rotatably joined to a separation piece at the first ends and each of the legs has an engagement piece at its second end. The engagement piece is configured to engage around the cylindrical instrument. Each engagement piece is oriented toward its corresponding leg at a fixed angle. The separation piece is configured to be connected to the receiver. The legs are adjusted such that the cylindrical instrument is received between the engagement pieces of the legs. The orientation of each of the engagement pieces to its corresponding leg positions the engagement pieces to contact the instrument at contact points in order that the receiver is located generally a fixed and known distance from the centerline regardless of the diameter of the instrument. The receiver communicating the position of the instrument to the computer such that the computer displays an image of the instrument relative to the image of the surgical site.

Certain embodiments of the present invention include a method for attaching a localizing device to a cylindrical surgical instrument. More specifically, the method includes providing a clip shaped attachment mechanism having legs with engagement pieces at a first end and the localizing device at a second end, and positioning the attachment mechanism about the instrument such that the instrument is received between the engagement pieces of the legs. The method further includes moving the engagement pieces about the instrument such that the engagement pieces contact the instrument at contact points in order that the localizing device is maintained a desired distance from a centerline of the instrument.

The foregoing summary, as well as the following detailed description of certain embodiments of the present invention, will be better understood when read in conjunction with the appended drawings. For the purpose of illustrating the invention, there is shown in the drawings, certain embodiments. It should be understood, however, that the present invention is not limited to the arrangements and instrumentality shown in the attached drawings.

DETAILED DESCRIPTION OF THE INVENTION

Figure 1:
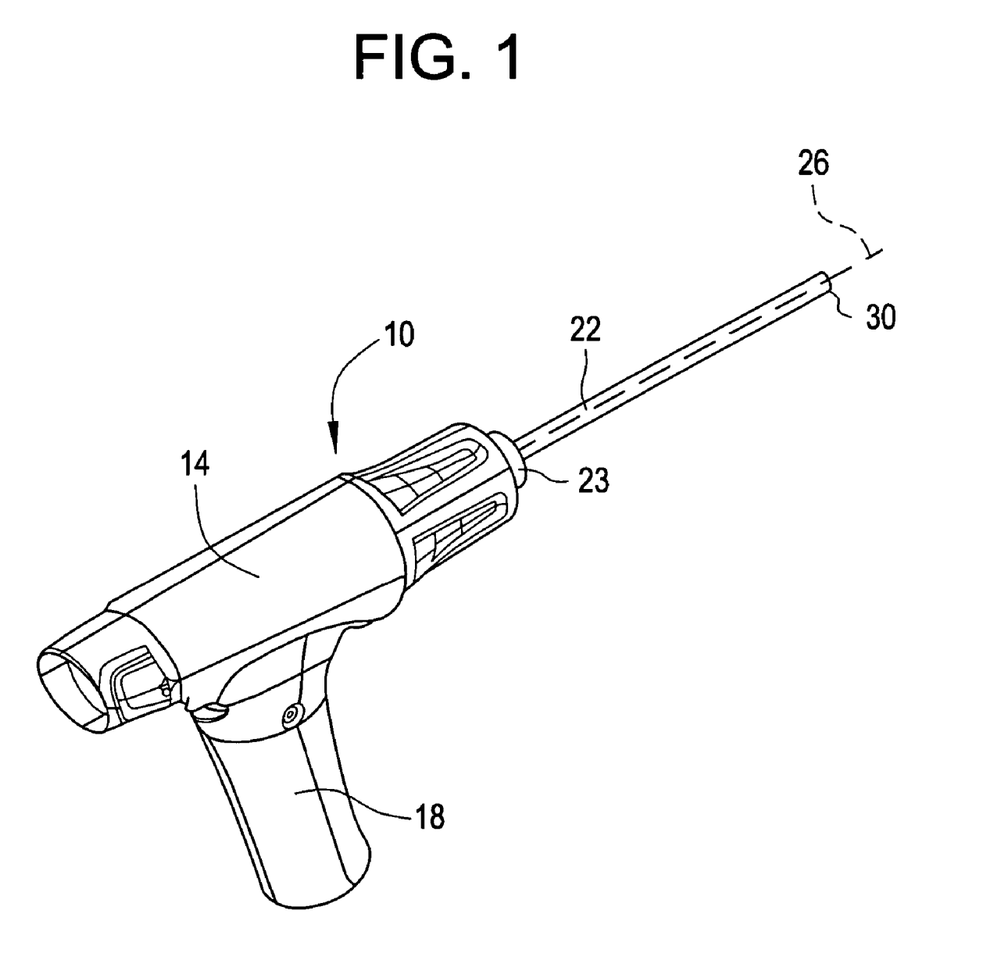
FIG. 1 is an isometric view of a conventional surgical instrument.

FIG. 1 is an isometric view of a conventional surgical instrument 10. The instrument 10 has a main body 14, a handle 18 and a working portion 22. For example, the instrument 10 may be a drill and the working portion 22 may be a drill bit. The working portion 22 extends from a front portion of the instrument 10 and may be removably connected thereto, e.g., via a chuck assembly 23. The working portion 22 is cylindrical and rotates during operation. The working portion 22 has a trajectory defined along a centerline 26 and has a distal tip 30. In at least one embodiment of the instrument, any number of different working portions 22 may be connected to the main body 14 during the course of a surgical procedure. For example, when the instrument is a drill, it may be necessary to use a variety of drill bits during a given surgical procedure. The different working portions may have varying lengths and diameters.

Figure 2:
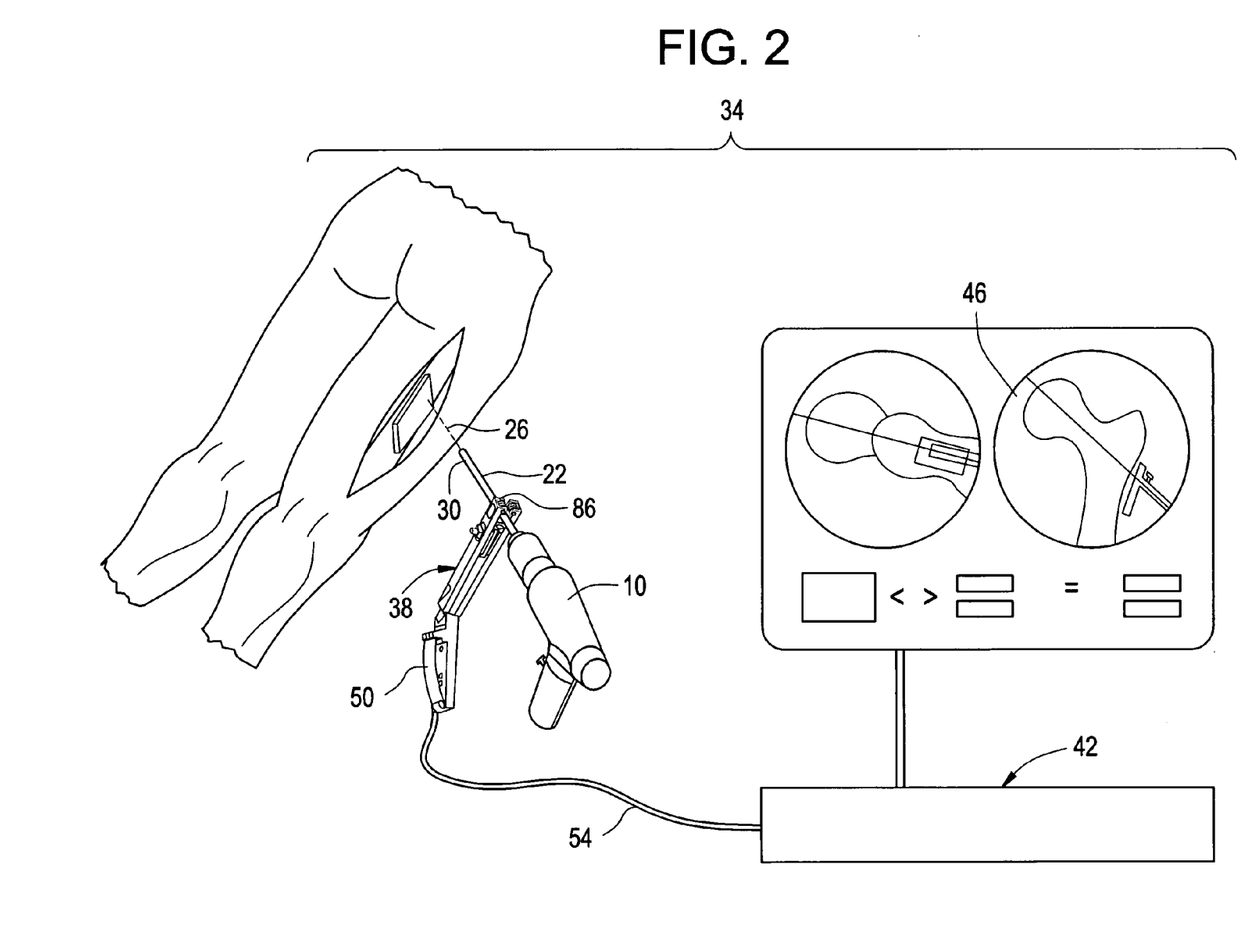
FIG. 2 is an isometric view of a surgical tracking system formed according to an embodiment of the present invention.

FIG. 2 is an isometric view of a surgical tracking system 34. The surgical tracking system 34 includes the working portion 22 of the instrument 10 extending from the instrument 10. An attachment mechanism 38 is connected to the working portion 22. The surgical tracking system 34 also includes a computer 42 and a screen 46. The screen 46 shows images of a surgical site where the instrument 10 is to be directed.

The attachment mechanism 38 carries a tracking element 50. In the illustrated embodiment the tracking system is an electromagnetic based tracking system and the tracking element 50 is in the form of an electromagnetic receiver. It will be appreciated, however, that the tracking element 50 could take a variety of forms depending on the specific tracking system that is employed. For example, the tracking system could be optical based, in which case the tracking element 50 could be an LED or a passive (reflective) tracking element. In the illustrated embodiment, the receiver 50 is connected to the computer 42 by a cord 54. The receiver 50 communicates with a transmitter (not shown) that is positioned proximate the surgical site in a fixed and known position relative to the surgical site. The transmitter is also connected to the computer 42. Thus, the receiver 50 and the transmitter communicate with each other and the computer 42 such that the computer 42 can calculate the position of the receiver 50 relative to the transmitter, and thus relative to the surgical site. Alternatively, the transmitter and/or receiver could use a wireless architecture.

Figure 3:
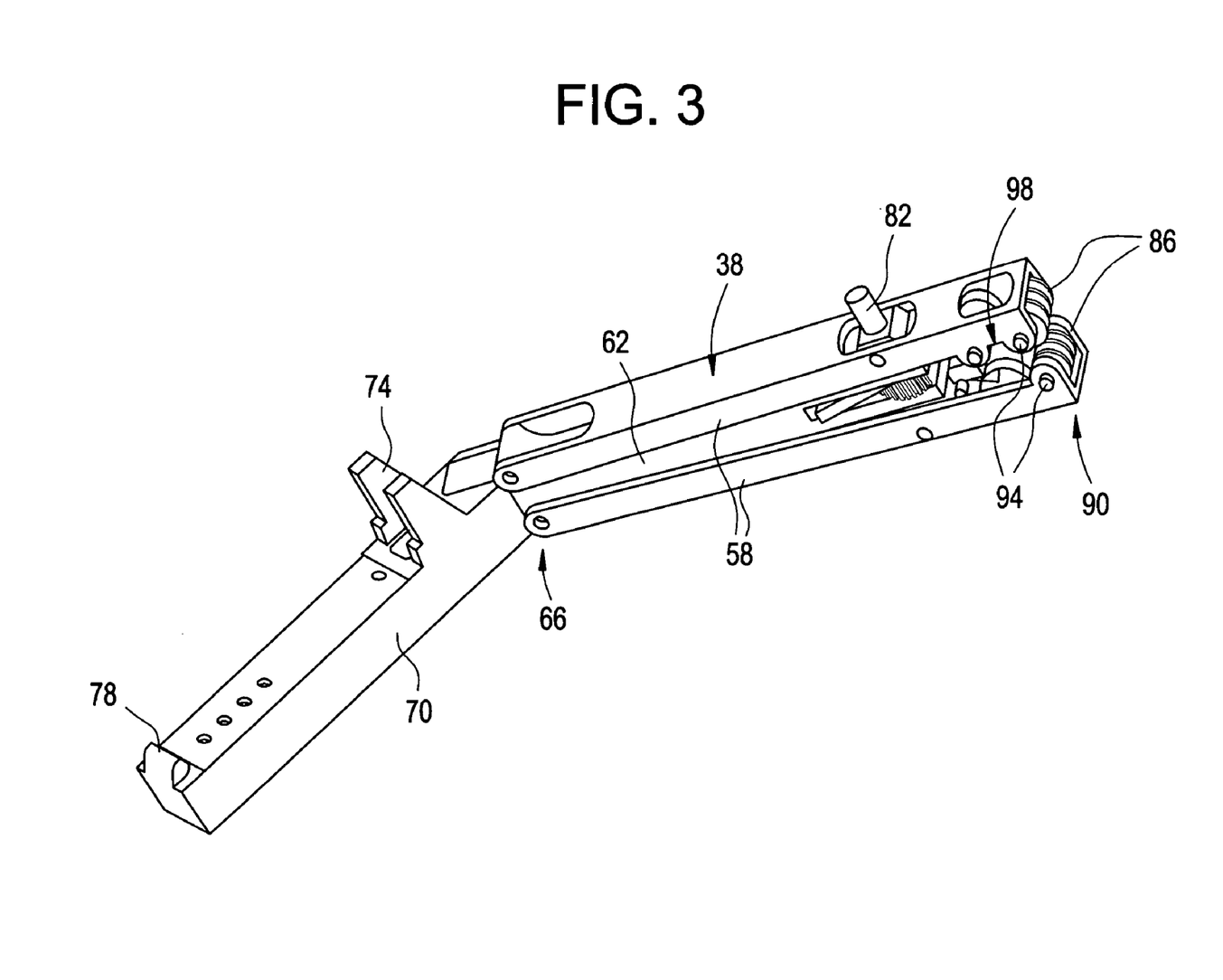
FIG. 3 is an isometric view of an attachment mechanism from FIG. 2.

FIG. 3 is an isometric view of the attachment mechanism 38. The attachment mechanism 38 is shaped like a clip and has two rectangular legs 58 positioned on opposite sides of a separation piece 62. The legs 58 are connected to the separation piece 62 at a first end 66 such that the legs 58 may rotate away from the separation piece 62 and each other at the first end 66. A receiver base 70 is rigidly connected to the separation piece 62 at the first end 66. The receiver base 70 has prongs 74 and a foot 78 on opposite ends that snapably receive the receiver 50 (FIG. 2) therebetween.

A screw 82 extends through the legs 58 and the separation piece 62 proximate where the legs 58 engage the working portion 22 of the instrument 10 (FIG. 2). The screw 82 can be adjusted such that the legs 58 are evenly moved closer to the separation piece 62, and thus each other, or such that the legs 58 are moved evenly away from the separation piece 62, and thus away from each other. The separation piece 62 is positioned between the legs 58 such that the legs 58 cannot be moved any closer to each other than the width of the separation piece 62.

Each leg 58 has rollers 86 located at a second end 90 thereof. The rollers 86 are rotatably retained on the legs 58 by pins 94 and are located on interior sides 98 of the legs 58. The rollers 86 on each leg 58 are a fixed distance from each other and are rotatable about the pins 94. Each leg 58 has a set of two or more rollers 86. The set of rollers 86 on each leg 58 is configured to engage the cylindrical working portion 22 (FIG. 2) of the instrument 10.

Figure 6:
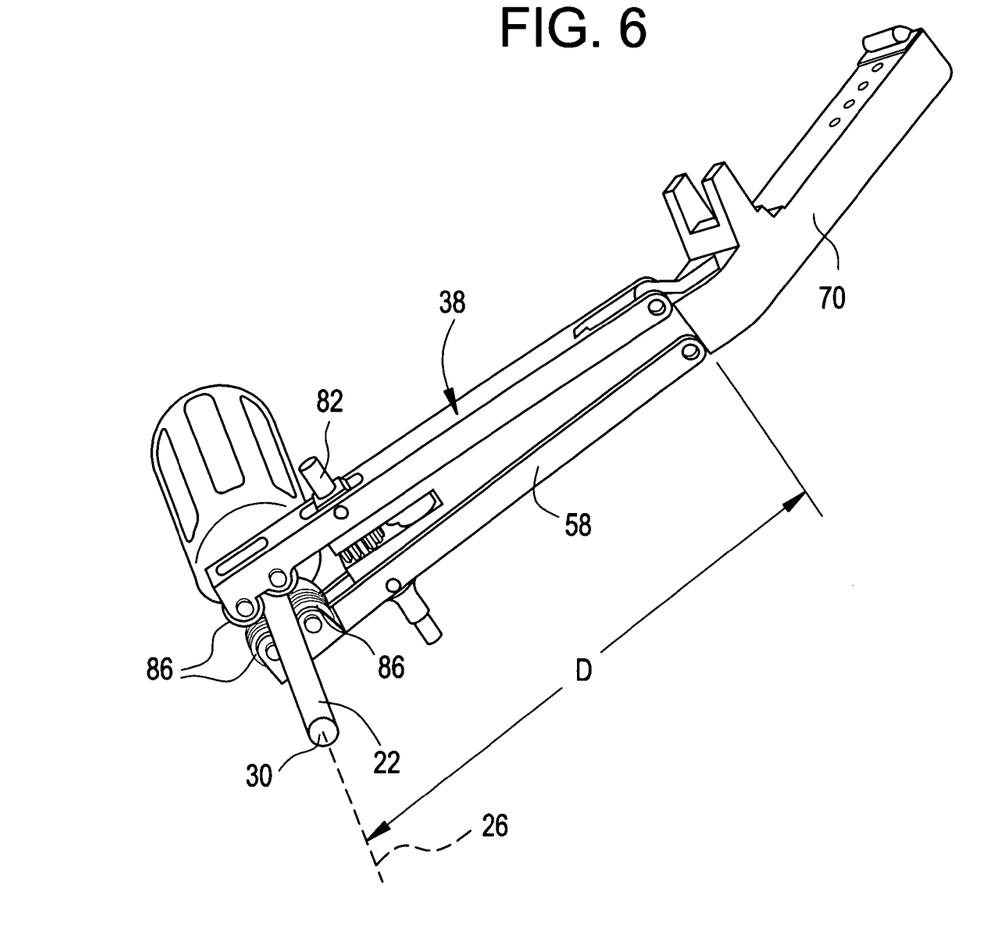
FIG. 6 illustrates an isometric view of the attachment mechanism and working portion of FIG. 2.

FIG. 6 illustrates an isometric view of the attachment mechanism 38 and working portion 22 of FIG. 2. In operation, the attachment mechanism 38 is connected to the working portion 22 by adjusting the screw 82 such that the legs 58 are rotated away from each other, or opened, until the gap between the rollers 86 on each leg 58 is large enough to receive the working portion 22. The working portion 22 is then positioned between the sets of rollers 86 on each leg 58 and the screw 82 is adjusted to rigidly tighten, or close, the legs 58 and rollers 86 about the working portion 22. Thus, the attachment mechanism 38 may be attached to the working portion 22 from the side and does not have to be slid over the distal tip 30. Therefore, the attachment mechanism 38 can be connected to a working portion 22 having an attachment of the distal tip 30. The legs 58 are fixed to the working portion 22 such that the attachment mechanism 38 does not slide perpendicularly to the centerline 26 of the working portion 22 and thus the receiver base 70 is maintained at a fixed and known distance from the centerline 26. The receiver base 70, and thus the receiver 50 (FIG. 2), is maintained a fixed and known distance D from the centerline 26 of the working portion 22. Likewise, the legs 58 are fixed to the working portion 22 such that the attachment mechanism 38 does not slide along the centerline 26 of the working portion 22 and thus the receiver 50 is maintained at fixed distance from the distal tip 30 of the working portion 22.

Ordinarily, the length of a clamp defined by legs such as those in the attachment mechanism 38 changes as a function of the cosine of the angle change. Thus, a four inch-long clamp opened up five degrees would create a length change, or shortening, of 0.015 inches. However, by cradling the working portion 22 within the four rollers 86, the positions of the four tangent contact points are adjusted such that the attachment mechanism 38 compensates for the length change. The geometry of the tangencies "shortens" the tool length at the same time that the cosine of the arc increases the tool length, and conversely, the geometry of the tangencies "lengthens" the tool length at the same time that the cosine of the arc decreases the tool length. The sets of rollers 86 are oriented on each leg 58 such that the distance D does not increase or decrease as the legs 58 are closed or opened, respectively. Thus, the receiver 50 is maintained the same known distance D from the centerline 26 of a working portion 22, regardless of the diameter of the working portion 22. Therefore, a surgeon can insert working portions 22 of different diameters throughout surgery without having to recalibrate the position of the receiver 50 with the centerline 26 of the new working portion 22. This adaptability of the attachment mechanism 38 can be better shown in the following geometric configurations.

Figure 4A:
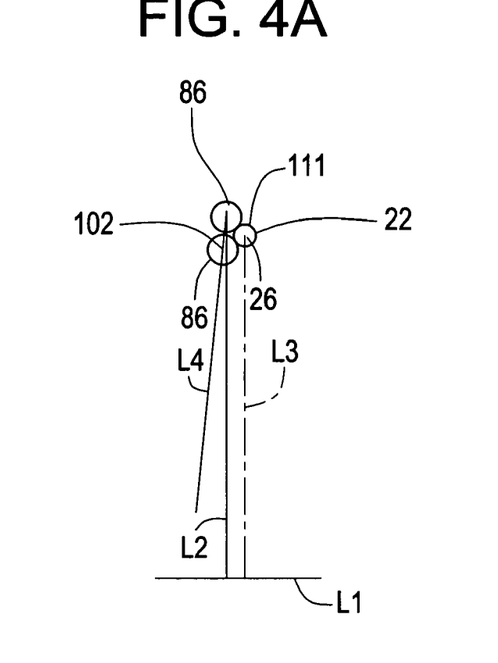
FIG. 4a is a geometric representation of rollers engaging a working portion having a first diameter.
Figure 4B:
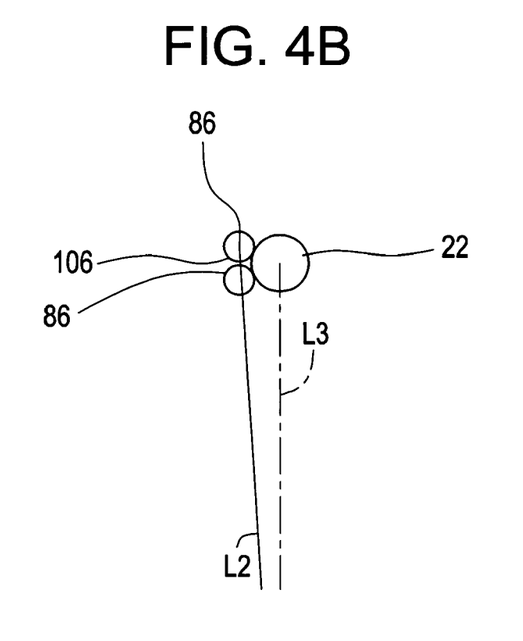
FIG. 4b is a geometric representation of rollers engaging a working portion having a second diameter.

FIGS. 4a and 4b are geometric representations of the rollers 86 of one of the legs engaging a working portion 22 having a first diameter of 0.250 inches and a working portion 22 having a second diameter of 0.750 inches, respectively. FIG. 4a shows the rollers 86 engaging a working portion 22 having a diameter of 0.250 inches. Line L1 represents a fixed plane along the receiver base 70 (FIG. 6). Line L2 represents a plane extending along a leg 58 (FIG. 6) from L1 to a centerline 102 of the proximal roller 86 and has a value of 4.0 inches. Line L3 represents a plane extending along the separation piece 62 (FIG. 6) from L1 to the centerline 26 of the working portion 22 and has a value of 4.17658 (or D1 as shown in FIG. 3). The centerlines 102 of the rollers 86 are aligned along a plane represented by line L4. As shown, L4 is oriented to L2 at an angle of 5.495, that is to say the centerlines 102 of the rollers 86 are oriented at an angle of 5.495 to the plane of the leg 58. The rollers 86 each have a diameter of 0.375 inches, the distance between L2 and L3 (the leg 58 and the separation piece 62) is 0.250 inches, the distance between the centerlines 102 of the rollers 86 is 0.400 inches, and the distance between Line L3 and the closest tangent of the distal roller 86 is 0.033 inches.

FIG. 4b shows the rollers 86 engaging a working portion 22 having a diameter of 0.750 inches. As shown, the distance D1 of line L3 is the same in FIG. 4b as it is in FIG. 4a despite FIG. 4b showing a working portion 22 having a diameter three times the size of the working portion 22 shown in FIG. 4a. Though the legs 58 (represented by line L2) shown in FIG. 4b have the same length of 4.0 inches and are opened further away from each other to accommodate the larger diameter of the working portion 22, the orientation of the rollers 86 relative to the leg 58 allows for the "extension" of the leg 58 such that the length of line L3 does not shorten. As shown, the distance between Line L3 and the closest tangent of the distal roller 86 has gone from 0.033 inches to 0.333 inches. Thus, the rollers 86 roll about a working portion 22 in order to position the rollers 86 about the working portion such that Line L3 (the distance from the centerline 26 to a fixed point on the receiver base 70) remains the same length regardless of the diameter of the working portion.

The attachment mechanism 38 does not alter its distance from the working portion 22 because the rollers 86 have differing tangential contact points that engage the working portions 22 of differing diameters. For example, in FIG. 4a, because the working portion has a smaller diameter of 0.250 inches, the rollers 86 have rolled clockwise about the working portion 22 such that the distal roller 86 overlaps about a far end 111 of the working portion 22. The rollers 86 thus accommodate for the "lengthening" of the attachment mechanism 38 caused by the legs 58 being brought close to each other. Alternatively, in FIG. 4b, because the working portion 22 has a larger diameter of 0.750 inches, the rollers 86 have rolled counter-clockwise about the working portion 22 such that the distal roller 86 is positioned more along a side 106 of the working portion 22. The rollers thus accommodate for the "shortening" of the attachment mechanism 38 caused by the legs 58 being separated from each other. In other words, the rollers 86 on the opposite legs 58 roll closer to each other when the diameter of the working portion 22 is smaller and the rollers 86 on the opposite legs 58 roll further away from each other when the diameter of the working portion 22 is greater.

Alternatively, the angles and lengths disclosed in FIGS. 4a and 4b may be altered to accommodate attachment mechanisms 38 having different leg 58 lengths or different sized rollers 86 or to accommodate working portions 22 having different sized diameters. Thus, the legs 58 may be any number of different lengths besides 4 inches, the angle of the planes of the rollers 86 to the plane of the leg 58 may be any number of different angles beside 5.495 degrees, etc. Different angles and lengths of the different components of the attachment mechanism 38 and working portion 22 may be arranged to correspond with each other to accommodate for changes in the length of the attachment mechanisms 38. Additionally, the geometric arrangement of the rollers 86, legs 58, and working portions 22 may result in different distances D1 for different working portions 22 where the variation in such distances D1 falls within an acceptable discrepancy range.

Returning to FIG. 2, in operation, images are taken of the surgical site with an imaging device such as an X-Ray, MRI, or CT scan. The images are stored on the computer 42 and can be reproduced on the screen 46. The transmitter is positioned proximate the surgical site in a fixed and known position relative to the surgical site. The surgeon selects a working portion 22, for example a drill bit, to be used with the instrument 10. The surgeon then connects the attachment mechanism 38 to the working portion 22 by securing the working portion 22 between the rollers 86. The receiver 60 connected to the attachment mechanism 38 communicates with the transmitter and the computer 42 such that the computer 42 can calculate the position of the receiver 50 relative to the transmitter and thus the surgical site. Because the receiver 50 is at a fixed and known distance D1 (FIG. 6) from the centerline 26 of the working portion 22 (regardless of the diameter of the working portion 22), the computer 42 can calculate the trajectory, of the working portion 22 relative to the surgical site.

After the attachment mechanism 38 is used to determine the trajectory of the instrument 10, the surgeon then calibrates the distal tip 30 of the working portion 22 by any number of ways known in the art. For example, the distal tip 30 may be registered at different points with other electromagnetic localizers that are in a known and fixed position relative to the transmitter or receiver 50. Specifically, the transmitter may include a dimple located in a fixed and known position such that the position of the receiver 50 may be known relative to the dimple as the transmitter communicates with the receiver 50. The surgeon may press the distal tip 30 of the working portion 22 into the dimple at a number of different orientations. Because the position of the receiver 50 is known relative to the trajectory and the dimple, the trajectory of the working portion 22 at each orientation is recorded by the computer 42 such that the point where all the recorded trajectories of the different orientations intersect represents the distal tip 30. Thus, the computer 42 calculates the position of the distal tip 30 relative to the receiver 50. Alternatively, the position of the distal tip 30 relative to the receiver 50 may be calculated by pressing the distal tip 30 into the dimple at only one orientation.

Once the computer 42 has calculated the position of the receiver 50 relative to the trajectory and distal tip 30 of the working portion 22, the computer 42 can project an image of the working portion 22 on the screen 46 relative to the surgical site. Thus, the surgeon can track the distal tip 30 and trajectory of the working portion 22 relative to the surgical site during surgery by viewing the screen 46. The surgeon can operate the instrument 10 while always being able to check that the working portion 22 is correctly entering the surgical site. Additionally, the surgeon can interchange working portions 22 during surgery without having to recalibrate the position of the receiver 50 relative to the trajectory of the working portion 22.

Figure 5:
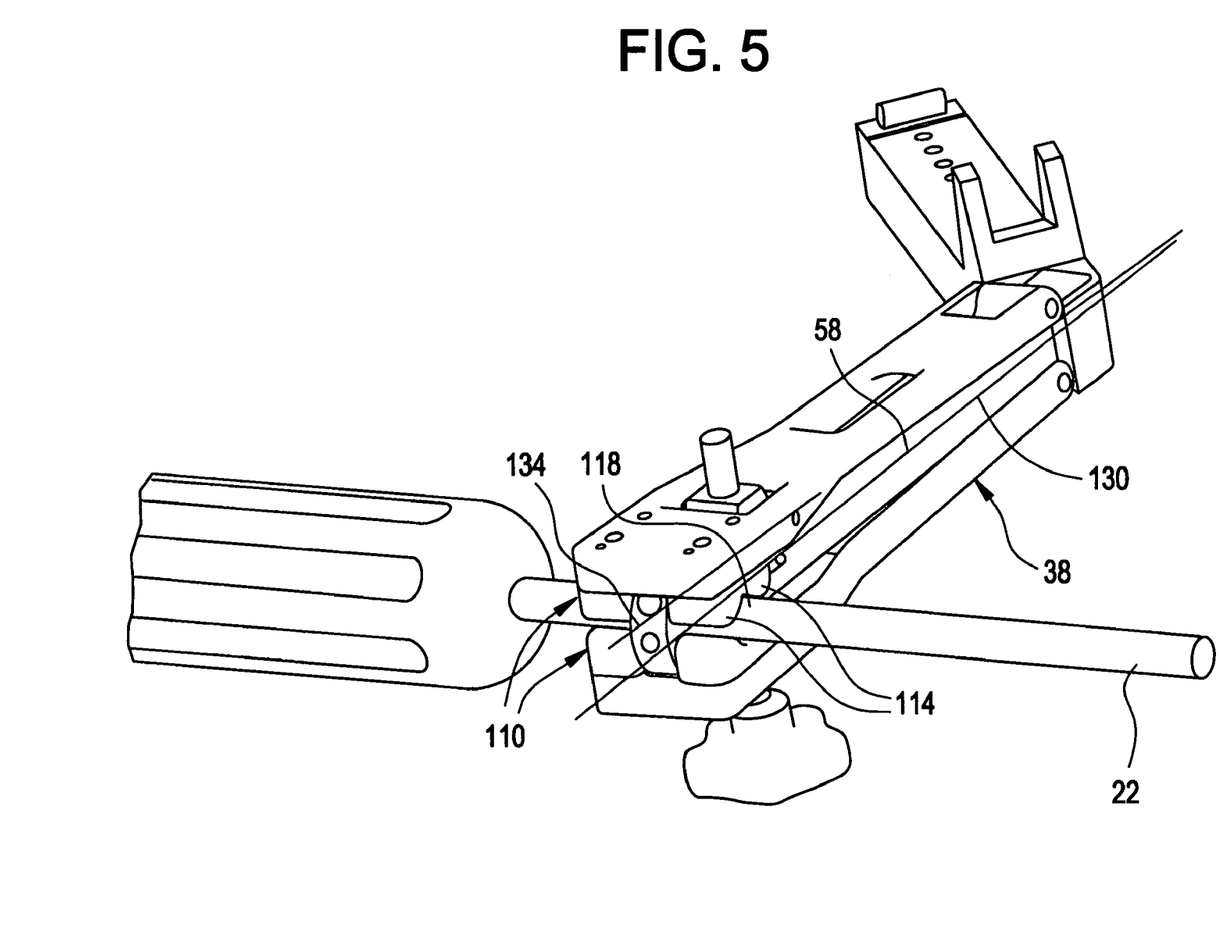
FIG. 5 illustrates an isometric view of an attachment mechanism formed according to an embodiment of the present invention.

FIG. 5 illustrates an isometric view of an attachment mechanism 38 of an alternative embodiment. In this embodiment, the attachment mechanism 38 has sliders 110 in place of the rollers 86 (FIG. 3). Each slider 110 has two rounded pads 114 separated by a gap 118 such that the working portion 22 is received within the gap 118 and engages contact points on the pads 114. The sliders 110 may be made of Teflon or any other material that will allow the slider 110 to slide along the working portion 22. Each slider 110 is aligned along a first plane 130 and each leg 58 is aligned along a second plane 134. The first plane 130 is oriented at an angle to the second plane 134. The pads 118 have differing tangential contact points that engage the working portions 22 of differing diameters such that the sliders 110 operate similarly to the rollers 86 in sliding about the working portion 22 to accommodate for changes in length of the attachment mechanism 38.

In an alternative embodiment, the attachment mechanism may be used with any number of other medical instruments besides a drill. Alternatively, the attachment mechanism may be used with non-medical instruments that are used as a part of a tracking system. Alternatively, the attachment mechanism may be used to connect any device a fixed distance from the centerline of any instrument having a cylindrical working portion. Alternatively, the attachment mechanism may carry a transmitter instead of a receiver. Alternatively, the attachment mechanism may be used with different tracking systems besides electromagnetic systems. For example, the attachment mechanism may be used with an optical system that utilizes LED's, optical reflectors, and cameras. Alternatively, the attachment mechanism may have other engagement pieces besides rollers or sliders that engage working portions at different contact points to accommodate the opening and closing of the attachment mechanism. Alternatively, the localize element may be mounted to one or both of the legs instead of being connected by a base and the separation piece.

The attachment mechanism of the different embodiments provides a number of benefits. First, the rollers/sliders attachment means that is oriented to the plane of the leg at an angle allows the attachment mechanism to be connected to cylindrical, rotating shafts of differing diameters without altering the distance or orientation of the receiver to the centerline of the shaft. Thus, the attachment mechanism provides a universal means for attaching a localizing device to an instrument and calibrating the localizing device with the trajectory and distal tip of the instrument. Therefore, localizing devices do not have to be integrated into every new instrument that is developed, rather the localizing device may be calibrated with any cylindrical instrument working portion regardless of size or make. Additionally, a surgeon does not have to recalibrate the receiver to find the trajectory of the working portion for each new working portion that is attached to the instrument. Also, the instrument itself does not need to have any localizing devices attached thereto nor does the surgeon have to insert the instrument into a cumbersome block each time the surgeon wishes to use a new working portion with the instrument. Further, the "clothes-pin" design of the attachment mechanism allows the attachment mechanism to clamp onto the side of an instrument instead of being slid over the distal tip. Thus, the attachment mechanism may be connected to instruments having large attachments at the distal end that the attachment mechanism could not be slid about.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. An attachment mechanism for attaching a component to a cylindrical instrument having a centerline, comprising:
    legs having respective first and second ends, said legs being pivotally connected relative to each other at said first ends such that said second ends of said legs can be pivoted away from each other and toward each other, said legs being configured to be connected to said component, each leg having an engagement piece at its second end, said engagement piece being configured to engage around said cylindrical instrument, each engagement piece being oriented toward its corresponding leg at a fixed angle, said orientation of each of said engagement pieces to its corresponding leg positioning said engagement pieces to contact said instrument at contact points in order that said component is located at a known and constant distance from said centerline regardless of the diameter of said instrument.

2. The attachment mechanism of claim 1, wherein each engagement piece comprises a pair of rollers and wherein said rollers roll about said instrument such that said rollers engage said instrument at contact points that maintain said component at said distance from said centerline of said instrument.

3. The attachment mechanism of claim 1, wherein each engagement piece comprises a slider having a pair of pads and wherein said pads slide about said instrument such that said pads engage said instrument at contact points that maintain said component at said distance from said centerline of said instrument.

4. The attachment mechanism of claim 1, wherein said engagement pieces contact said instrument at different contact points such that said component is located generally said distance from said centerline.

5. The attachment mechanism of claim 1, wherein each engagement piece comprises a pair of rollers, said rollers on said opposite legs rolling along said instrument away from each other in order to maintain said component said distance away from said centerline of said instrument.

6. The attachment mechanism of claim 1, wherein each engagement piece is a slider having a set of pads, said pads on said opposite legs sliding along said instrument away from each other in order to maintain said component said distance away from said centerline of said instrument.

7. The attachment mechanism of claim 1, further including a separation piece joined to said legs at said first ends, wherein said separation piece includes a screw that extends through said separation piece and said legs, said screw engaging said legs such that rotation of said screw in a first direction causes said legs to evenly move closer to each other and rotation in a second direction causes said legs to evenly move away from each other.

8. The attachment mechanism of claim 1, further including a separation piece joined to said legs at said first ends, wherein said separation piece includes a base that receives said component such that said component is maintained said distance from said centerline of said instrument.

9. The attachment mechanism of claim 1, further including a separation piece joined to said legs at said first ends, wherein said separation piece is connected to a component base that snapably receives said component such that said component is located a fixed and known distance away from said centerline of said instrument.

10. The attachment mechanism of claim 1, wherein said engagement piece comprises a pair of rollers, said rollers on said opposite legs rolling along said instrument toward each other in order to maintain said component said distance away from said centerline of said instrument.

11. The attachment mechanism of claim 1, wherein said attachment mechanism is configured to connect an electromagnetic receiver to a surgical drill.

12. A computer assisted surgical tracking system, comprising:
    a surgical drill having a cylindrical instrument with a centerline;
    an electromagnetic receiver;
    a computer that displays an image of a surgical site; and
    an attachment mechanism, said attachment mechanism including legs having respective first and second ends, said legs being rotatably joined to a separation piece at said first ends and each of said legs having an engagement piece at its second end, said engagement pieces being configured to engage around said cylindrical instrument, each engagement piece being oriented toward its corresponding leg at a fixed angle, said separation piece being configured to be connected to said receiver, said legs being adjusted such that said cylindrical instrument is received between said engagement pieces of said legs, said orientation of each of said engagement pieces to its corresponding leg positioning said engagement pieces to contact said instrument at contact points in order that said receiver is located generally a fixed and known distance from said centerline regardless of the diameter of said instrument, said receiver communicating the position of said instrument to said computer such that said computer displays an image of said instrument relative to said image of said surgical site.

13. The computer assisted surgical tracking system of claim 12, wherein each engagement piece comprises a pair of rollers and wherein said rollers roll about said instrument such that said rollers engage said instrument at contact points that maintain said receiver at said distance from said centerline of said instrument.

14. The computer assisted surgical tracking system of claim 12, wherein each engagement piece comprises a slider having a pair of pads and wherein said pads slide about said instrument such that said pads engage said instrument at contact points that maintain said receiver at said distance from said centerline of said instrument.

15. The computer assisted surgical tracking system of claim 12, wherein said instrument comprises a plurality of instruments having different diameters, said engagement pieces contacting said plurality of instruments at different contact points such that said receiver is located generally said distance from said centerlines of said plurality of instruments.

16. The computer assisted surgical tracking system of claim 12, wherein each engagement piece comprises a pair of rollers and wherein said instrument includes a first shaft having a first diameter and a second shaft having a second diameter, said second diameter being greater than said first diameter, said rollers on said opposite legs rolling along said second shaft away from each other in order to maintain said receiver said distance away from said centerline of said second shaft, said rollers on said opposite legs rolling along said first shaft toward each other in order to maintain said receiver said distance away from said centerline of said first shaft.

17. The computer assisted surgical tracking system of claim 12, wherein each engagement piece comprises a slider having a pair of pads and wherein said instrument includes a first shaft having a first diameter and a second shaft having a second diameter, said second diameter being greater than said first diameter, said pads on said opposite legs sliding along said second shaft away from each other in order to maintain said receiver said distance away from said centerline of said second shaft, said pads on said opposite legs sliding along said first shaft toward each other in order to maintain said receiver said distance away from said centerline of said first shaft.

18. The computer assisted surgical tracking system of claim 12, wherein said separation piece includes a screw that extends through said separation piece and said legs, said screw engaging said legs such that rotation of said screw in a first direction causes said legs to evenly move closer to each other and rotation in a second direction causes said legs to evenly move away from each other.

19. The computer assisted surgical tracking system of claim 12, wherein said separation piece is connected to a receiver base that snapably receives said receiver such that said receiver is located said fixed and known distance away from said centerline of said instrument.

20. A method for attaching a localizing device to a cylindrical surgical instrument, comprising:

providing a clip shaped attachment mechanism having legs with engagement pieces at a first end and said localizing device at a second end;

positioning said attachment mechanism about said instrument such that said instrument is received between said engagement pieces of said legs; and moving said engagement pieces about said instrument such that said engagement pieces contact said instrument at contact points in order that said localizing device is maintained a desired distance from a centerline of said instrument.

* * * * *